United States Patent
Ramani et al.

(10) Patent No.: US 6,275,559 B1
(45) Date of Patent: Aug. 14, 2001

(54) METHOD AND SYSTEM FOR DIAGNOSING FAULTS IN IMAGING SCANNERS

(75) Inventors: Vipin Kewal Ramani, Niskayuna; Rasiklal Punjalal Shah, Latham; Peter Michael Edic, Albany; Shankar Visvanathan Guru, Clifton Park; Abdalmajeid Musa Alyassin, Niskayuna, all of NY (US); Randal Vincent Dusing, Mukwonago, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/415,409

(22) Filed: Oct. 8, 1999

(51) Int. Cl.[7] ........................................................ A61B 6/03
(52) U.S. Cl. ................................................. 378/4; 378/207
(58) Field of Search .............................. 378/4, 207, 901

(56) References Cited

U.S. PATENT DOCUMENTS 4,853,946 * 8/1989 Elliott et al. ............................. 378/4
6,105,149 * 8/2000 Bonissone et al. ..................... 714/26

* cited by examiner

Primary Examiner—David V. Bruce
(74) Attorney, Agent, or Firm—David C. Goldman; Jill M. Breedlove

(57) ABSTRACT

A system is provided for identifying faults in a non-OEM computed tomography system having components in connection with the detectors to reconstruct an image. Then, correlation values are derived from baseline reference data files and current data files collected after a fault is suspected in the CT system. The correlation values are compared against a threshold to identify suspect detectors and a pattern recognition algorithm is applied to determine if the suspect detectors are faulty or if one of the components processing the output signals has failed. If baseline files are unavailable, the identification of faulty components is accomplished by performing correlation between the current data files and average profile values.

31 Claims, 4 Drawing Sheets

METHOD AND SYSTEM FOR DIAGNOSING FAULTS IN IMAGING SCANNERS

FIELD OF THE INVENTION

The present invention generally relates to systems for diagnosing imaging scanners, and, in particular, to a system for diagnosing faults in imaging scanners without utilizing proprietary diagnostic information.

BACKGROUND OF THE INVENTION

Hospitals and other medical facilities utilize a variety of imaging scanner equipment, including computed tomography (CT) scanners, magnetic resonance (MR) imaging systems, and x-ray apparatus to produce images of internal parts of patients under examination. These imaging scanners are produced by various manufacturers, such as General Electric, Picker, Phillips, etc. In many instances, medical imaging scanners are maintained by service companies that do not have direct association with the manufacturer of the equipment being serviced. In such servicing arrangements, the original manufacturer of the imaging system will often remove all tools, including proprietary diagnostic software programs from the imaging system that are used to help service its equipment. This leaves the servicing company with the challenging task of attempting to maintain medical imaging equipment without having access to the proprietary information necessary to service such equipment. Because medical imaging equipment is extremely complex and intricate, it is extremely difficult to service these machines when there are no diagnostic tools available.

SUMMARY OF THE INVENTION

Thus, there is a particular need for a diagnostic system that is capable of identifying problems in imaging scanners without having access to the proprietary diagnostic software programs.

The present invention is directed to a method and system for identifying faults in an imaging system, such as a non-original equipment manufacture (non-OEM) scanners, having a number of detectors generating intensity measurement signals representative of the intensity of radiation impinging thereupon, and a number of subsystem components coupled to the detectors for reconstructing images from the detector signals received. The present diagnostic system collects data file output by at least one of the components and uses the collected data file to identify possible faulty detectors and other faulty subsystem components. Identification of faulty detectors and faulty subsystem components may be accomplished by performing a correlation operation on the current data file collected after a fault is suspected. The correlation values derived by the correlation operation are used to identify which detectors and subsystem components are suspected of faulty operations.

DETAILED DESCRIPTION

A variety of imaging systems are used in hospitals and other medical facilities to provide images of internal parts, such as computed tomography scanners, magnetic resonance (MR) imaging systems, and x-ray apparatus. The present invention is directed to a diagnostic system for identifying failed subsystem components in imaging systems.

Figure 3:
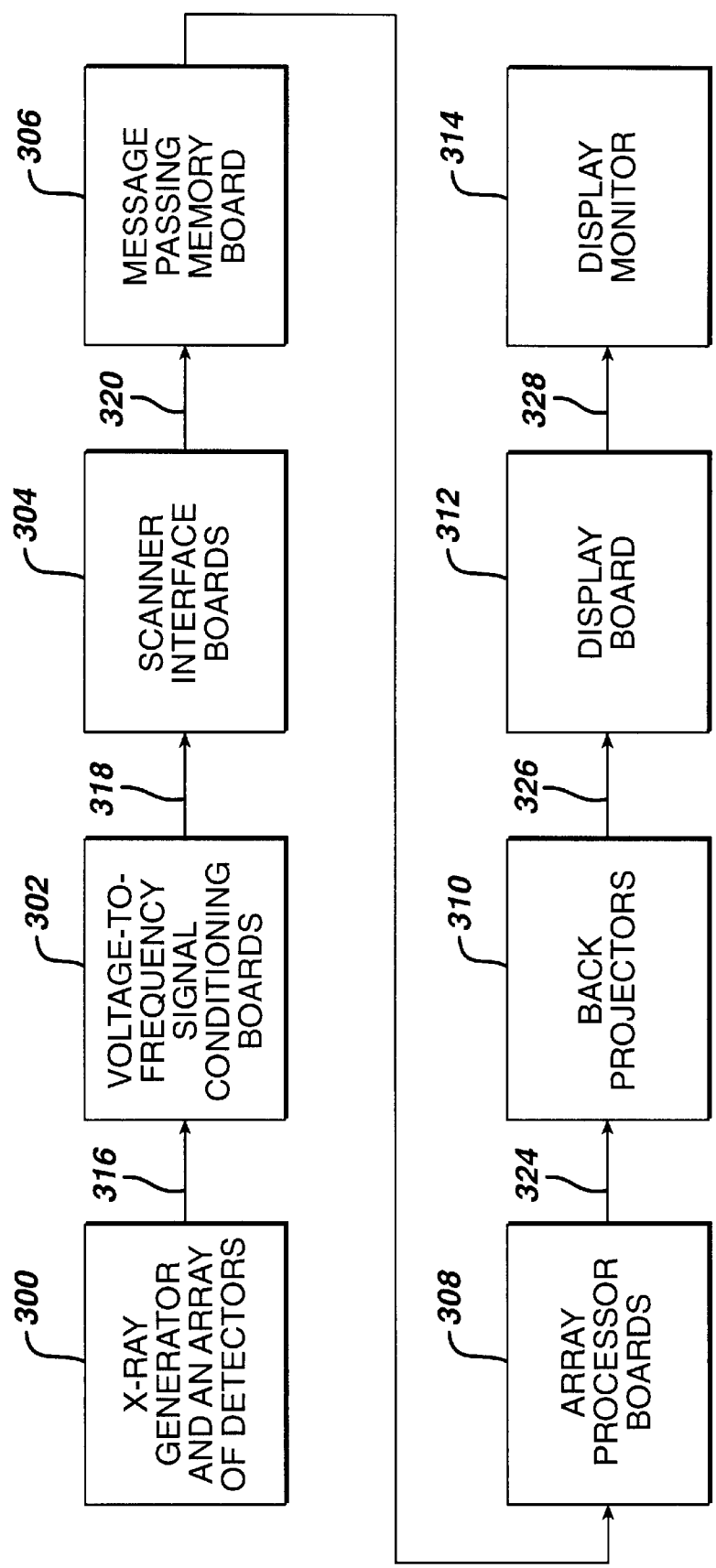
FIG. 3 is a block diagram illustrating a data flow in a CT imaging system.

Referring to FIG. 3, a number of replaceable subsystem components of a computed tomography (CT) imaging system are shown, among any one of which failures are liable to occur. The CT imaging system includes a radiation source, such as an X-ray generator, which projects a fan beam of radiation. The fan beam passes through a patient under examination and impinges on a portion of detectors 300. Each detector produces output signals that are proportional to the X-ray intensity impinging at the detector, the intensity of which is indicative of radiation absorptive or transmissive properties of the patient. The output signals 316 are then transmitted to a number of electronic components for reconstructing an image across the anatomical plane defined by the scanning x-ray fan beam. Each component receives data from a previous component corresponding to a previous stage of the imaging chain and processes the received data to generate new data which is used by a subsequent component. In general, the output signals 316 from the detectors are collected, normalized, corrected for the polychromaticity of the X-ray beam, and filtered before an actual image is reconstructed.

For ease of description and as an illustrative example, the diagnostic system will be described in terms of a fourth generation CT imaging system and more specifically to CT imaging systems manufactured by Picker, namely IQ and PQ models. However, it is to be understood that the diagnostic system in accordance with the present invention may be applied to any imaging scanner system modality, independent of manufacturer, provided that access to data at intermediate stages of the imaging process is available. In some of the existing fourth generation CT imaging systems, many detectors are utilized, i.e., on the order of 1200 and 4800 detectors, which may be arranged in a stationary ring configuration. Also included in the fourth generation CT imaging system is an x-ray generator which may be housed in a rotating scan frame. The angular orientation of the scan frame is incremented with respect to the stationary detector ring to a number of different scan frame angles, i.e., on the order of 4800 different angular positions. At each scan frame angle, intensity measurements from a group of the detectors illuminated by the x-ray beam are acquired. This set of intensity measurement data at a scan frame angle is referred to as a "profile." A number of profiles are collected along different scan frame angles to form a tomographic profile set. The tomographic profile set is later used to reconstruct a cross-sectional image of the plane through which the fan beams pass.

In addition to the detectors, the CT imaging system further includes a number of subsystem components in connection with the detectors, each of which is associated with one of the image reconstruction stages. The image reconstruction begins with voltage-to-frequency signal conditioning (VFSC) boards 302. The VFSC boards 302 receive the analog output signals 316 from the array of detectors 300 and digitizes the detector signals and outputs in the form of 16 bit words via a scanner interface cable to scanner interface (SIF) boards 304. The primary function of the SIF board 304 is to store data as it is received and reformat the 16 bit words into 32 bit words for faster travel across the multibus II backplane in an operator console. A message passing memory (MPMB) board 306 receives the source fan (SRCF) data 320 from the SIF board and serves to shuffle the SRCF data into detection fan (DETF) data 322. The DETF data 322 is then transmitted to array processor (AP) boards 308 which correct and filter the DETF data 322. The back projectors 310 back project the filtered DETF data 324 received from the AP boards 308 using a pipeline architecture data flow format. Next, a display board 312 converts digital data 326 from the back projectors 310 into analog image signals 328 for display on a display monitor 314.

Failures are liable to occur in any one of the detectors and/or electronic boards mentioned above; for example, it is possible that one or more of the detectors 300 may malfunction and no longer produce meaningful intensity measurements. It is also possible that one of the components 302–312 for reconstructing images may malfunction to the point where the outputs 318–328 from such component may be inaccurate or unreliable. To produce accurate images of internal parts of patients under examination, it is important to provide a diagnostic system to facilitate identifying faulty components of CT imaging systems and instruct field engineers in an appropriate course of action. The diagnostic system of the present invention analyzes data collected at output of one or more of the subsystem components to provide a list of possible faulty components. Typically, CT imaging systems allow for collection of data files output by each individual component described above. By the term "data file" it will be understood that reference is made to a complete set of profiles collected at different scan angles required to form a cross-sectional image, where each respective profile contains the processed output signals from a group of detectors at a particular scan angle.

Figure 1:
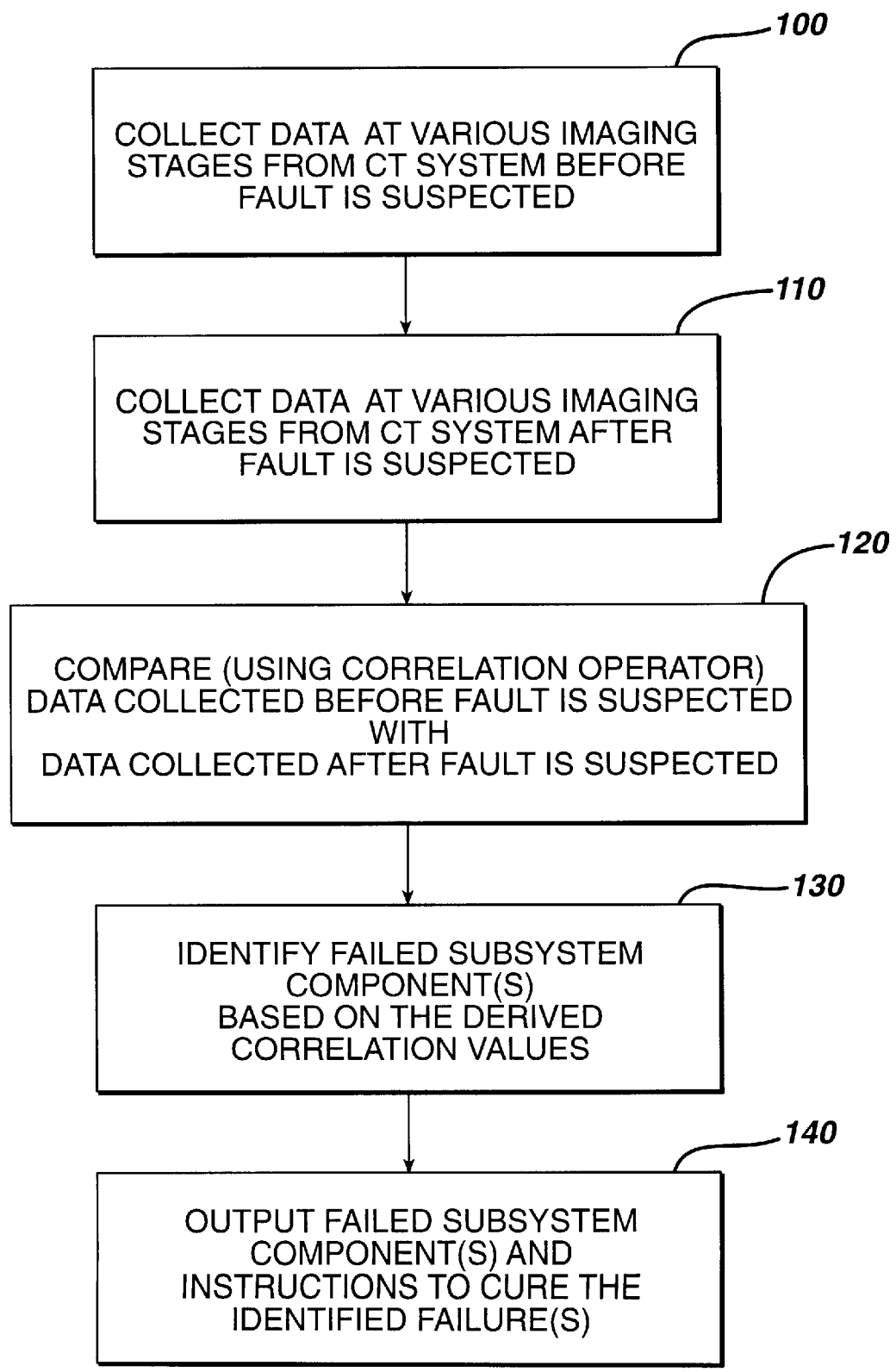
FIG. 1 is a flow diagram illustrating the general steps involved in diagnosing a CT imaging system in accordance with one embodiment of the present invention.

Referring to FIG. 1, a flowchart diagram illustrating the general steps involved in the diagnostic system, according to the present invention, is shown. In step 100, baseline reference data files are collected at one or more of the imaging stages while the CT system is functioning properly. Prior to collecting the baseline data files, the CT imaging system is preferably set at predetermined settings, i.e., slice thickness, tube voltage and tube current. The baseline data files may be acquired using a calibration phantom placed on the gantry table near the center of the field of view for an axial scan. The calibration phantom is typically used with calibration routines to calibrate the CT system, and it may be, for example, cylindrical in shape and filled with a material of known density, such as water.

After a fault is suspected in the imaging system, current data files are collected at various imaging stages in step 110 using the same calibration phantom with the imaging system set at the same settings as used in step 100. In this regard, the data files collected before and after suspected failure may be compared against each other to identify faulty signals and corresponding detectors and subsystem components that are responsible for ouputting such faulty signals. In step 120, the baseline reference data files (collected in step 100) are compared against the current data files (collected in step 110) using a correlation operator to provide automated fault identification. The results of the correlation operation are used in step 130 to identify failed subsystem components. Finally, in step 140, the diagnostic system of the present invention informs a user of the possible failed components and recommended repair procedure actions based upon the identified failures. Steps 120–140 may be embodied in the form of an application program processed or executable set of instructions running on a computer. The computer implementing the diagnostic program of the present invention may be any computer capable of performing sequential program executions, including portable computers used by field engineers, or a computer provided at the operator console.

In general, failures are most likely to occur in one or more of the detectors and/or daughtercards of the VFSC boards. Accordingly, the diagnostic program may first analyze the collected data files to determine if the failure condition is caused by either faulty detectors or faulty VFSC daughtercards before proceeding with the diagnosis of other subsystem components. This can be accomplished by analyzing one of the current data files, such as the current DETF data file. If baseline reference data files are available, a mathematical correlation operation is performed between the baseline DETF data file and the current DETF data file. The data files may be organized in the form of a matrix of measurement values, such as pixel values. In step 120, the correlation operation returns correlation values, each of which characterizes the working state of a corresponding detector. The correlation values are obtained by correlating all pixel values $P_{ik}$ of the current DETF data file with the pixel values $B_{ik}$ of the baseline reference DETF data. The correlation vector $C_i$ is as follows:

$$C_i = corr(P_{ik}, B_{ik})$$

where $P_{ik}$ is the pixel value of the current data file for the $i^{th}$ detector and $k^{th}$ profile and $B_{ik}$ is the pixel value of the baseline reference data file.

Each individual correlation value represents how closely the processed output signal data of an individual detector matches with data that would be output if the imaging system was operating faultlessly. In step 130, the correlation values derived in the correlation vector are then compared against a threshold to identify faulty components. The correlation value associated with each of the detectors is examined sequentially, and if the correlation value is below a threshold, the corresponding detector is flagged as suspect. In this manner, the characteristics of each detector are assessed, and a list of suspect detectors is generated.

Prior to performing correlation operations between baseline reference and current data files, the data files are preferably parsed and formatted into a specific form. Once data files have been collected from various imaging stages, each individual data file is parsed to remove portions of the data file that are not needed for reconstructing an image. The removed portions of data may include, for example, headers, calibration data, position of the gantry, numbers assigned to different detectors and other miscellaneous information. Once the portions of the data file have been removed, a pattern of an object being scanned is identified. Because the circular calibration phantom is used to generate these data files, it is assumed that the object being scanned is circular. In order to aid the correlation operation, each individual profile within the data file is normalized such that the center of each profile image is centered with respect to centers of other profile images. Each individual profile is collected into different bins such that each bin contains processed output detector signals obtained at a scan angle. Thus, each data file includes a number of bins to hold the entire set of profiles necessary to reconstruct a cross-sectional image. The data in each individual bin may be formatted such that the processed output signals are arranged in the same order as the corresponding detectors responsible for generating such output signals. In general, one could format data from any CT machine into this format. The reformatted current data file is then compared to the reformatted baseline reference data files to identify detectors and other components whose output signals are suspect.

Figure 2:
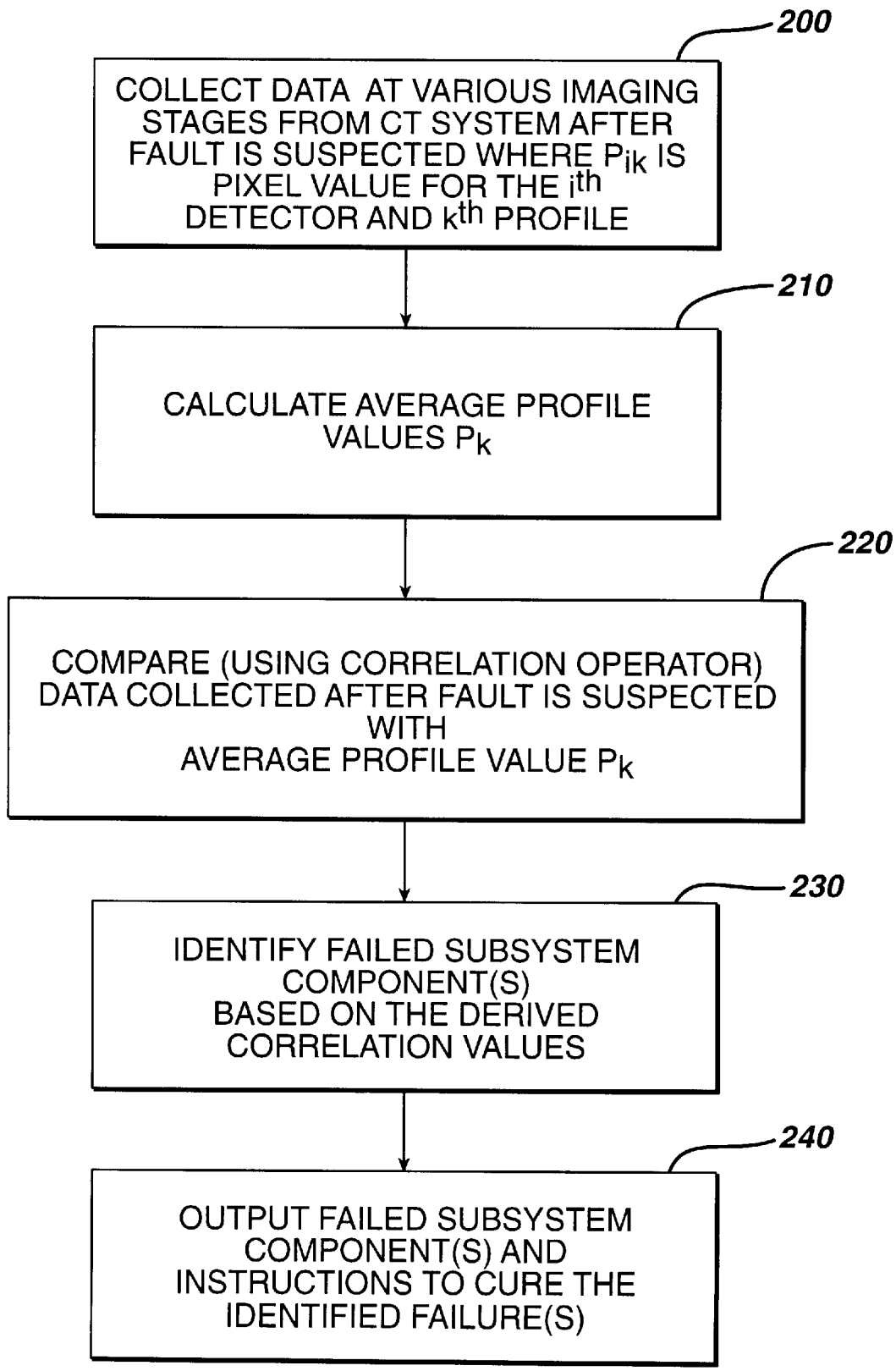
FIG. 2 is a flow diagram illustrating the general steps involved in diagnosing a CT imaging system in accordance with another embodiment of the present invention.

In many circumstances, the baseline standard data files may not be available. According to one aspect of the invention, the imaging system may be diagnosed even if there are no baseline reference data files available with which correlation operations can be performed. Referring to FIG. 2, a flow diagram illustrates the general steps required to diagnose the imaging system when baseline standard data files are unavailable for performing correlation operations. In this case and in step 200, current data files are collected at various imaging stages after fault is suspected with a calibration phantom placed near the center of the field of view for an axial scan. The phantom is preferably placed on the gantry table with the position of the table adjusted so that the axial laser light used for patient orientation during scanning is placed at the midsection of the calibration phantom. Each of the current data files include a complete set of profiles necessary for reconstructing a cross-sectional image, where each profile contains intensity measurement signals output by the detectors collected at a particular scan angle. Faulty components are identified by performing a correlation operation between the current data file and average profile values, where each average profile value is derived by averaging pixel values of detectors at each respective profile. In step 210, average profile values $P_k$ are calculated as follows:

$$P_k = \frac{\sum_{i=1}^{m} P_{ik}}{i}$$

where $P_{ik}$ is the pixel value for the $i^{th}$ detector and $k^{th}$ profile, and the value for i is either 1200 or 4800 depending on whether the imaging system is a Picker IQ or PQ system.

Next, in step 220, correlation values are obtained by correlating all pixel values $P_{ik}$ with average profile values $P_k$. The correlation vector is given by $$C_i = corr(P_{ik}, P_k)$$

In step 230, the values derived in the correlation vector are then checked against a threshold to identify one or more components which are suspected of faulty operation. Finally, in step 240, the diagnostic system displays possible failed components and recommends repair procedure actions based on the identified failures.

To identify failures caused by other subsystem components, a pattern recognition algorithm is applied to the suspect detectors. Certain patterns of suspect detectors may be attributable to a fault elsewhere in the CT system. If the pattern of the suspect detectors matches one of the predetermined patterns, this may indicate that the faulty signals are caused by failure in one of the subsystem components, for example failure in one of the daughtercards residing on VFSC boards. When one of the daughtercards malfunctions, the signature in the current data file is such that the faulty output signals are spaced apart in equal intervals. Thus, patterns of faulty output signals in the current data file may be utilized to identify certain subsystem components that are malfunctioning.

In one embodiment, the diagnostic program may utilize a database for storing pattern information for comparing with the identified suspect detectors. Once all detectors have been tested, the diagnostic system is configured to search through the database and generate recommended repair procedures based on one or more patterns matched by the suspect detectors.

The patterns described below are specific to a fourth generation Q-series Picker CT machine, i.e., Picker IQ and PQ systems. However, in general, one would apply pattern recognition specific to a particular manufacturer of imaging equipment since the patterns are hardware specific.

As an example, the imaging system being diagnosed may be a Picker IQ imaging system which includes three VFSC boards. Twenty-five daughtercards (each containing electronics for 4 channels) reside on each of the VFSC boards, where each individual daughtercard may be removed and replaced with another daughtercard. The IQ system has 1200 detectors, each of which is associated with one of 75 daughtercards. More specifically, 4 detectors are multiplexed into each channel on the daughtercards, each multiplexed detector being separated by 300 detector numbers. If one of the daughtercards malfunctions on the IQ system, the signature in the data file is such that suspected detectors are 300 detectors apart. Thus, if the output signal data associated with detector numbers 1, 301, 601 and 901 is faulty, this indicates that the daughtercard, responsible for channeling output signals from those detectors, is malfunctioning.

As another example, the imaging system being diagnosed may be a Picker PQ imaging system which has twelve VFSC boards, 4800 detectors; each respective detector is associated with one of 300 daughtercards. In the PQ system, one of the daughtercards corresponds, for example, to detector numbers 1, 1201, 2401 and 3601. Thus, if a set of four suspect detectors is found, where each suspect detector is separated by 1200 detectors, this indicates that a channel on a daughtercard on one of the VFSC boards has failed. By performing the appropriate modulo arithmetic, it is possible to assess the VFSC board number, the daughtercard number, and the channel number on the daughtercard. The graphical user interface is used to suggest that such VFSC board or daughtercard needs to be replaced.

The pattern recognition algorithm is also used to identify failure caused by one of the detector modules, each of which is comprised of a set of ten adjacent detectors. If a pattern of ten adjacent suspect detectors whose starting detector number is a multiple of ten, this may indicate that a corresponding detector module has failed. In such case, the field engineer is requested to replace the detector module, as outlined by messages from the graphical user interface.

If the correlation values of the correlation vector do not match any of the prescribed patterns described above, this may indicate individual detector failure. In this case, the detector module corresponding to the faulty detector can be replaced. Alternatively, the detector number can be included in the system configuration file of faulty detector numbers. The CT imaging system uses the faulty detector numbers to ignore data generated by such faulty detectors and to substitute a value derived by averaging two adjacent detectors of each respective defective detector. The diagnostic program identifies the single detector failure and provides instructions to a user via the user interface to either replace the detector module or include the detector number in the system configuration file of faulty detector numbers.

Once the proper repair procedure has been executed, data files are once again collected using the circular water phantom to ensure that the correct failure mode has been identified. If an image quality issue still exists, the data files generated at various points of the imaging chain are once again analyzed to identify additional faulty components.

Figure 4:
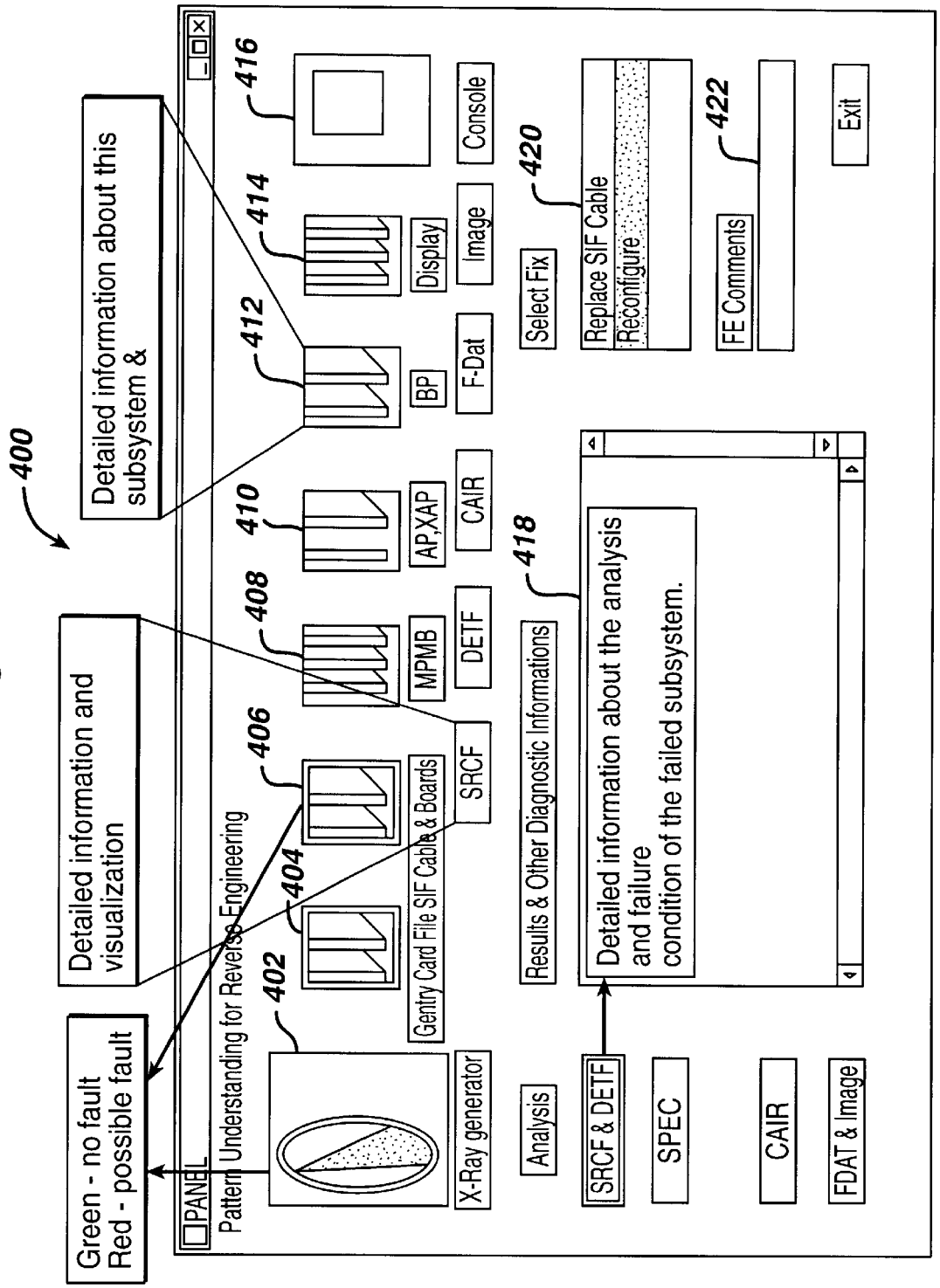
FIG. 4 is a view of a user interface displayed by the diagnostic system of the present invention.

Referring to FIG. 4, a user interface 400 used to display faulty components is shown. The user interface 400 includes icons 402–416 representing various subsystem components. The user interface allows an operator to initiate testing of a particular component by selecting the icon corresponding to such component. An indication as to whether a particular component is functioning properly or improperly may be represented symbolically; for example, a green box may be drawn around an icon to indicate that the corresponding component is properly functioning, and a red box may be drawn around an icon to indicate possible malfunction. The user interface further includes several window fields. The first window field 418 is used to communicate detailed information about the analysis and failure condition of the failed subsystem component. The diagnostic system is configured to generate a recommended repair procedure based on faulty detectors and suspect subsystem components identified by performing the correlation operation and the pattern recognition algorithm. The suggested repair procedure actions are displayed in the second window field 420. During diagnosis of the imaging system, the operator may enter comments into the third window field 422, such as a brief description of the possible cause of the problem and acknowledgment that the problem has been resolved.

Referring back to FIG. 3, if the analysis of current DETF data file does not indicate failure, this may indicate that the previous components 300, 302, 304 and 306 are functioning properly, and the system failure is caused by components 308, 310, 312 and 314 subsequent to the detector fan data. In such case, data is collected at other subsequent points in the imaging chain 324, 326 and 328. Once the data has been collected, the component causing the problem is determined by identifying the component that receives good input data but outputs bad data. For example, if the correlation values associated with the current DETF data do not indicate failure, the outputs generated by one of the subsequent components, e.g., the AP boards, are compared to a corresponding reference data file to determine if the AP boards are functioning properly.

While the foregoing preferred embodiments of the invention have been described and shown, it is understood that variations and modifications, such as those suggested and others within the spirit and scope of the invention, may occur to those skilled in the art to which the invention pertains. The scope of the present invention accordingly is to be defined as set forth in the appended claims.

What is claimed is:

1. A diagnostic system for identifying faults in an imaging system having a plurality of detectors generating output signals and a plurality of components in connection with the detectors for reconstructing images from the output signals generated by the plurality of detectors, said diagnostic system comprising:

a memory storing at least one current data file which includes data output by one of the plurality of components after a fault is suspected in the imaging system; and a processor in connection with the memory for processing said at least one current data file to identify faulty detector and component.

2. The diagnostic system of claim 1, wherein said diagnostic system is used to identify faults in a non-OEM imaging system by only utilizing non-proprietary information contained in said at least one current data file.

3. The diagnostic system of claim 1, wherein said at least one current data file includes at least one of the following: detector output signal data, source fan data, detector fan data, filtered data, convolved data, and image data.

4. The diagnostic system of claim 1, wherein the imaging system is a computed tomography system having a radiation source projecting a fan beam of radiation and the output signals generated by the detectors are proportional to the intensity of radiation impinging at each respective detector.

5. The diagnostic system of claim 4, wherein the at least one current data file includes a plurality of profiles collected at a plurality of scan angles, each respective of said plurality of profiles including measurement values representative of intensity signals from the detectors, wherein said plurality of profiles are used to reconstruct a cross-sectional image.

6. The diagnostic system of claim 4, wherein the at least one current data file includes a plurality of current measurement values $P_{ik}$, each of the measurement values $P_{ik}$ corresponding to the signals generated by the $i^{th}$ detector at $k^{th}$ profile.

7. The diagnostic system of claim 6, wherein the processor is configured to calculate average profile values $P_k$ which are calculated as follows:

$$P_k = \frac{\sum_{i=1}^{m} P_{ik}}{i}.$$

8. The diagnostic system of claim 7, wherein the processor is configured to obtain correlation values by correlating the measurement values $P_{ik}$ with the average profile values $P_k$, wherein the correlation values are calculated as follows:

$$C_i = corr(P_{ik}, P_k).$$

9. The diagnostic system of claim 8, wherein the correlation values are compared against a threshold to identify detectors which are suspected of faulty operations.

10. The diagnostic system of claim 9, wherein the processor is configured to determine whether a predetermined pattern of suspect detectors has occurred based on the correlation values, and further wherein the processor is configured to identify a faulty component which corresponds to such predetermined pattern.

11. The diagnostic system of claim 6, wherein the memory stores at least one baseline reference data file which includes data output by one of the plurality of components while the imaging system is operating properly.

12. The diagnostic system of claim 11, wherein the at least one baseline reference data file includes a plurality of baseline reference measurement values $B_{ik}$, each of the baseline reference measurement values $B_{ik}$ corresponding to the signals generated by the $i^{th}$ detector at $k^{th}$ profile.

13. The diagnostic system of claim 12, wherein the processor is configured to obtain correlation values by correlating the current measurement values $P_{ik}$ with the baseline reference measurement values $B_{ik}$, wherein the correlation values are calculated as follows:

$$C_i = corr(P_{ik}, B_{ik}).$$

14. The diagnostic system of claim 13, wherein the correlation values are compared against a threshold to identify detectors which are suspected of faulty operations.

15. The diagnostic system of claim 14, wherein the processor is configured to determine whether a predetermined pattern of suspect detectors has occurred based on the correlation values, and further wherein the processor is configured to identify a faulty component which corresponds to such predetermined pattern.

16. The diagnostic system of claim 1, further comprising a user interface in connection with the processor for displaying possible faulty components in the computed tomography system and recommend repair procedure actions based on identified failures.

17. A diagnostic system for identifying faults in a non-OEM imaging system without utilizing proprietary information, said non-OEM imaging system having a plurality of detectors generating output signals and a plurality of components in connection with the detectors for reconstructing images from the output signals generated by the plurality of detectors, said diagnostic system comprising:

means for collecting at least one current data file including data output by one of the plurality of components after a fault is suspected in the imaging system, said at least one current data file including processed output signals generated by said plurality of detectors at a plurality of scan angles;

means for obtaining at least one baseline reference data file including data that would be output by said one of the plurality of components if the imaging system is operating faultlessly;

means for comparing said at least one current data file with said at least one baseline reference data file using a correlation operation to produce correlation values; and means for identifying faulty detector and component based on the correlation values.

18. The diagnostic system of claim 17, wherein said at least one current data file includes at least one of the following: detector output signal data, source fan data, detector fan data, filtered data, convolved data, and image data.

19. The diagnostic system of claim 17, wherein said at least one baseline reference data file is obtained while the imaging system is operating properly by collecting data output by said one of the plurality of components.

20. The diagnostic system of claim 17, wherein:

said at least one current data file comprises a plurality of current measurement values $P_{ik}$, each of the measurement values $P_{ik}$ corresponding to processed signals originally output by the $i^{th}$ detector at $k^{th}$ profile;

said at least one baseline reference data file is obtained by calculating average profile values $P_k$ which are calculated as follows:

$$P_k = \frac{\sum_{i=1}^{m} P_{ik}}{i}$$

said correlation values are obtained by correlating the measurement values $P_{ik}$ with the average profile values $P_k$, wherein the correlation values are calculated as follows:

$$C_i = corr(P_{ik}, P_k).$$

21. A diagnostic method for identifying faults in an imaging system having a plurality of detectors generating output signals and a plurality of components coupled to the detectors for reconstructing images from the output signals generated by the detectors, said diagnostic method comprising the steps of:

collecting at least one current data file output by one of the plurality of components after a fault is suspected in the imaging system; and processing said at least one current data file to identify possible faulty detectors and components.

22. The diagnostic method of claim 21, wherein said diagnostic method is used to identify faults in a non-OEM imaging system by only utilizing non-proprietary information extracted from said at least one current data file collected.

23. The diagnostic method of claim 21, wherein the imaging system is a computed tomography system having a radiation source projecting a fan beam of radiation and the output signals generated by the detectors are proportional to the intensity of radiation impinging at each respective detector.

24. The diagnostic method of claim 23, wherein the at least one current data file includes a plurality of profiles collected at a plurality of scan angles, each respective of said plurality of profiles including output signals received from the detectors at a corresponding scan angle, wherein said plurality of profiles is used to reconstruct a cross-sectional image.

25. The diagnostic method of claim 23, wherein the at least one current data file includes a plurality of current measurement values $P_{ik}$, each of the measurement values $P_{ik}$ corresponding to the signals generated by the $i^{th}$ detector at $k^{th}$ profile.

26. The diagnostic method of claim 25, further comprising the steps of:

calculating average profile values $P_k$ which are calculated as follows:

$$P_k = \frac{\sum_{i=1}^{m} P_{ik}}{i}$$

calculating correlation values by correlating the measurement values $P_{ik}$ with the average profile values $P_k$, wherein the correlation values are calculated as follows:

$$C_i = corr(P_{ik}, P_k)$$

comparing said correlation values against a threshold to identify detectors which are suspected of faulty operations.

27. The diagnostic method of claim 26, further comprising the steps of:

determining whether one of a plurality of predetermined pattern of suspect detectors has occurred; and identifying a faulty component which corresponds to the predetermined pattern.

28. The diagnostic method of claim 21, further comprising the step of collecting at least one baseline reference data file output from one of the plurality of components while the imaging system is operating properly.

29. The diagnostic method of claim 28, wherein the at least one baseline reference data file includes a plurality of baseline reference measurement values $B_{ik}$, each of the baseline reference measurement values $B_{ik}$ corresponding to the signals generated by the $i^{th}$ detector at $k^{th}$ profile.

30. The diagnostic method of claim 29, further comprising the steps of:

calculating correlation values by correlating the current measurement values $P_{ik}$ with the baseline reference measurement values $B_{ik}$, wherein the correlation values are calculated as follows:

$$C_i = corr(P_{ik}, B_{ik})$$

comparing the correlation values against a threshold to identify detectors which are suspected of faulty operations.

31. The diagnostic method of claim 30, further comprising the steps of:

determining whether one of a plurality of predetermined pattern of suspect detectors has occurred; and identifying a faulty component which corresponds to such predetermined pattern.

* * * * *